(12) United States Patent
French et al.

(10) Patent No.: US 6,200,292 B1
(45) Date of Patent: Mar. 13, 2001

(54) SUCTION AND IRRIGATION HANDPIECE AND TIP

(75) Inventors: Glen French, Barrington, RI (US); Stephen Albrecht, South Walpole, MA (US); Roger Darois, Foster, RI (US); Robert Sakal, Riverside, RI (US); Laurence Tremaine, West Warwick, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 08/665,467

(22) Filed: Jun. 18, 1996

(51) Int. Cl.[7] .............................. A61M 1/00; A61M 37/00
(52) U.S. Cl. .............................................. 604/131; 604/35
(58) Field of Search ................................. 604/131, 132, 604/133, 146, 151, 153, 43, 35, 39, 310, 313, 355, 268, 27, 28

(56) References Cited

U.S. PATENT DOCUMENTS

| Re. 28,405 | 5/1975 | Sollerud . | |
|---|---|---|---|
| 517,274 | 3/1894 | Gullings . | |
| 906,711 | 12/1908 | McClung Hill et al. . | |
| 1,178,898 | 4/1916 | Young . | |
| 2,531,793 | 11/1950 | Sulek . | |
| 2,771,072 | 11/1956 | De Montauge . | |
| 3,735,751 | 5/1973 | Katz | 128/2 F |
| 4,776,840 | * 10/1988 | Freitas et al. | 604/33 |
| 4,810,194 | 3/1989 | Snedden . | |
| 5,046,486 | * 9/1991 | Grulke et al. | 604/131 X |
| 5,302,124 | 4/1994 | Lansing et al. . | |
| 5,354,267 | * 10/1994 | Niermann et al. | 604/32 |
| 5,470,305 | * 11/1995 | Arnett et al. | 601/161 |
| 5,488,949 | 2/1996 | Kreifels et al. . | |
| 5,527,275 | * 6/1996 | Ginsberg | 604/131 X |
| 5,735,833 | * 4/1998 | Olson | 604/289 |
| 5,746,721 | * 5/1998 | Pasch et al. | 604/153 |
| 5,941,851 | * 8/1999 | Coffey et al. | 604/131 |

FOREIGN PATENT DOCUMENTS

| 2171312 | 8/1986 | (GB) . |
|---|---|---|
| WO9501759 | 1/1995 | (WO) . |

* cited by examiner

*Primary Examiner*—Sharon Kennedy
(74) *Attorney, Agent, or Firm*—Arthur Z. Bookstein (57) ABSTRACT

A medical suction and irrigation apparatus includes a suction/irrigation tip removably connected to a conventional suction/irrigation handpiece. Suction is provided through a suction tube which has a bypass conduit in the tip. The bypass conduit is directly connectable to a suction source so that aspirated debris passes through the tip to the suction source. The suction tube thus prevents aspirated debris from entering the conventional suction tube in the handpiece and contaminating the handpiece. The suction tube is also designed to have a maximum size to prevent the tip from clogging. The tip also has an irrigation tube for directing irrigation liquid to the irrigation site, and a connector which connects the irrigation tube to the handpiece so that the handpiece pumps fluid through the tip in a conventional manner. A flexible splash shield, slidably mounted to the irrigation tube, confines irrigation fluid to the local site.

14 Claims, 6 Drawing Sheets

SUCTION AND IRRIGATION HANDPIECE AND TIP

FIELD OF THE INVENTION

This invention relates generally to medical irrigation systems and, more particularly, to hand-held medical irrigation devices that have a tip with suction and irrigation channels.

BACKGROUND OF THE INVENTION

Irrigation devices are in common use in a variety of non-surgical environments, such as nursing homes and other long-term care facilities, where they are used to treat bed sores and other injuries that are accessible externally about a patient. These devices generally comprise an irrigation handpiece and accompanying irrigation tip that direct irrigation liquid from an irrigation source to an irrigation site. Effective treatment often requires that the injured site be irrigated several times.

Conventional irrigation and suction devices have a combination suction and irrigation tip that can be detachably connected to a handpiece having both irrigation and suction lumens. The free end of the tip has a conical splash shield that, during use, is pressed against and about the irrigated region to confine irrigation liquid (e.g., saline) to that region. A typical tip is shown in U.S. Pat. No. 4,692,140 (Olson). The Olson tip has an outer (suction) tube, an inner (irrigation) tube coaxially aligned with the suction tube, and a web (referred to as "pegs" in Olson) that supports the distal end of the irrigation tube within the suction tube. The annular space between the tubes provides a suction pathway for biological debris aspirated from the irrigation site. Aspirated biological debris is drawn through the suction pathway to the suction lumen in the handpiece, from which it flows through a connecting tube to a debris collection chamber.

One problem with such devices is that the biological debris ingested into the handpiece suction lumen (from the irrigation site) may contain infectious bacteria that could contaminate the handpiece. The handpiece can thus become septic and may create an undesirable risk of reinfection to the patient if it is reused. Accordingly, although irrigation handpieces with detachable tips are available, there has been a resistance to their use because the handpieces are relatively expensive and can only be used once. The preferred treatment is to to bathe the patient in a warm whirlpool bath instead of locally irrigating the injury with an irrigation handpiece and tip. This alternative treatment method is inefficient, however, since it is time consuming and treats both injured and uninjured parts of the patient's body.

Another difficulty with the foregoing coaxial tip is that the suction pathway can clog easily with aspirated biological debris because it has a relatively small cross-sectional dimension. The web also appears to further obstruct debris drawn toward the annular suction pathway since it partially covers the open distal end of the pathway.

A flexible splash shield that is permanently fastened to the distal end of the outer suction tube also presents problems. More particularly, when the irrigation tip must be positioned very close to the irrigation site, it may be necessary to cut off the end of the shield along one of several circumferential ring guides. In addition to being time consuming and cumbersome, the structure of the tip is permanently altered. A new tip must be used to irrigate a larger local injury site.

In addition, it is common during use for irrigation fluid and biological debris to escape from the splash shield because, for example, the irrigation surface may not be smooth or the attendant may inadvertently move the handpiece while irrigating. This can cause the debris and irrigation liquid to splash onto the handpiece and/or attendant, consequently contaminating the handpiece and exposing the attendant to infection.

It therefore is among the general objects of the invention to provide an improved suction/irrigation tip that avoids contamination of the handpiece.

SUMMARY OF THE INVENTION

In accordance with one aspect of the invention, the suction lumen in a detachable suction and irrigation tip is configured so that aspirated fluid and debris are passed directly to an external suction source when the tip is used with a conventional handpiece having both suction and irrigation lumens. No portion of the suction lumen in the tip is in fluid communication with the suction lumen in the handpiece. However, the irrigation lumen in the handpiece is in fluid communication with the irrigation lumen in the tip so that irrigation can pass through the handpiece and tip in normal fashion.

In accordance with another aspect of the invention, the suction and irrigation lumens in the tip are arranged coaxially with the inner tube defining the suction lumen and the annular lumen between the inner and outer tubes defining the irrigation lumen. The annular lumen terminates in an annular end wall that includes a number of circumferentially spaced outlet apertures through which irrigation liquid is emitted. Since the cross-sectional dimension of the suction lumen is greater than the radial dimension of the surrounding annular lumen, the risk of that lumen being clogged by debris is reduced.

In accordance with yet another aspect of the invention, a flexible splash shield is slidably mounted on the tip. This enables the distal end of the suction and irrigation tubes to be positioned directly against the irrigation site without having to cut the shield.

In accordance with still another aspect of the invention, the tip is provided with a protective covering having one end that is heat sealed to the tip and another end that is open. When the tip is connected to a handpiece, the covering is sized to fit loosely about the handpiece and may extend past the bottom of the handpiece. The covering protects the handpiece and the attendant from debris that may splash from the irrigation site.

It is among the objects of the invention to provide combination suction and irrigation tip that it detachably connectible to a handpiece and in which biological debris aspirated through the suction lumen bypasses the handpiece.

Another object of the invention is to provide an improved combination suction and irrigation tip that may be detachably connected to an irrigation handpiece in which the risk of the handpiece becoming contaminated with biological debris is reduced.

BRIEF DESCRIPTION OF THE DRAWINGS

The foregoing and other objects and advantages of the invention will be appreciated more fully from the following further description thereof with reference to the accompanying drawings wherein.

DESCRIPTION OF THE ILLUSTRATIVE EMBODIMENT

Figures 1, 2:
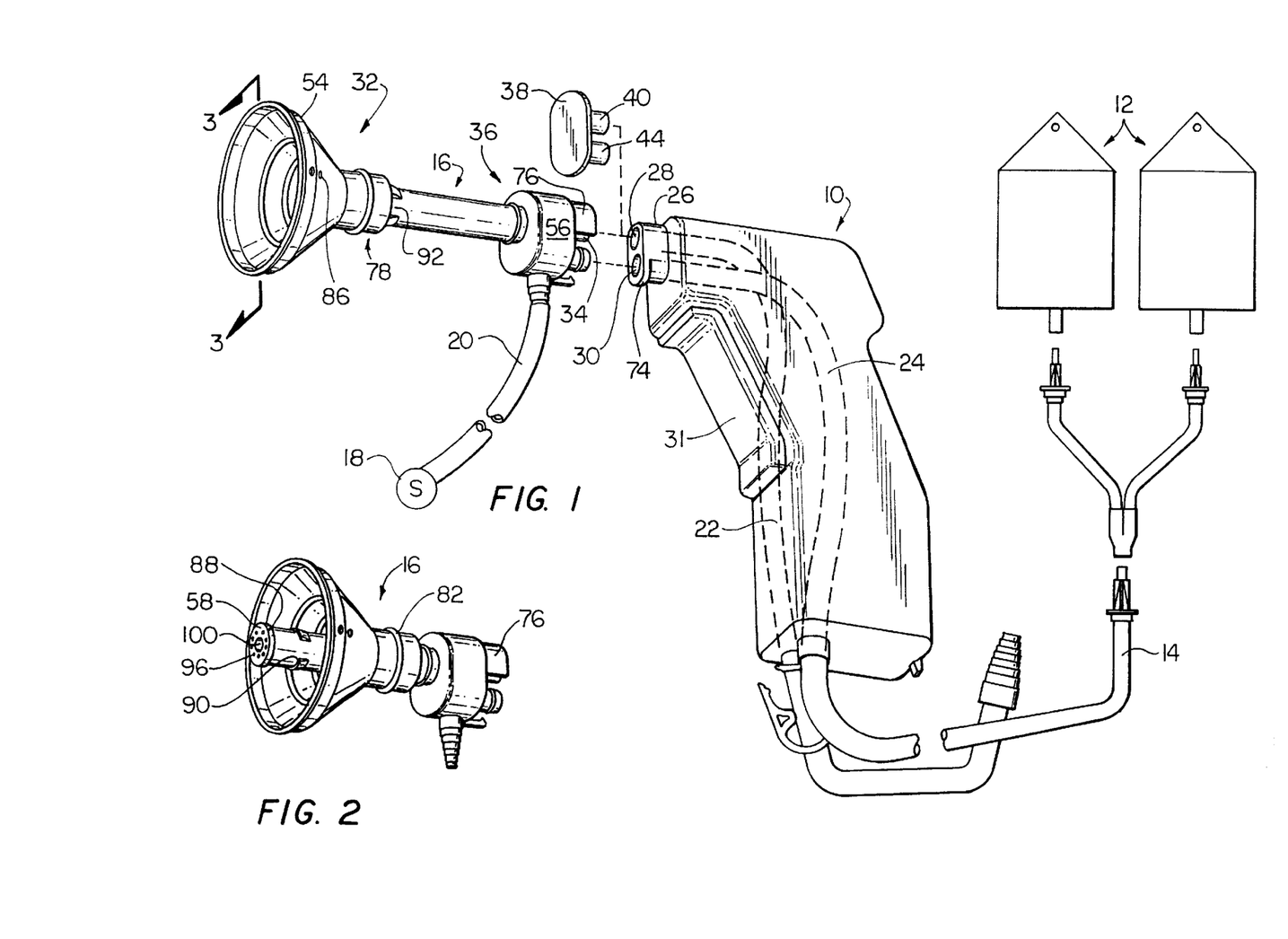
FIG. 1 is a perspective view of the irrigation system in accordance with the invention.
FIG. 2 is a perspective view of the suction irrigation tip with the splash shield retracted.

FIG. 1 illustrates the main components of the suction and irrigation system, which includes a conventional handpiece 10 connected to a reservoir bag 12 by flexible irrigation tubing 14, and a combination suction and irrigation tip 16 detachably connectible to the handpiece 10. Such a handpiece may also include a suction tube 20 extending into the interior of the handpiece 10 which can be connected to a suction source 18 (e.g., wall suction) to aspirate debris. As described in detail below, when the inventive tip 16 is connected to the handpiece 10, a suction bypass is provided that diverts aspirated debris away from the interior of the handpiece 10, thus reducing the risk of contaminating the handpiece 10. Irrigation fluid (e.g., saline) is provided by the bag 12, from which it is pumped through the handpiece 10 and tip 16, to the irrigation site.

The handpiece 10 may be a Simpulse Solo™ suction irrigator (available from C.R. Bard, Inc. of Murray Hill, N.J.) which has a self contained pump, battery, and motor, (omitted for clarity) such as that described in more detail in co-pending U.S. patent application No. 08/389,155, now U.S. Pat. No. 5,746,721, assigned to C.R. Bard, Inc. A suction lumen 22 and an irrigation lumen 24, shown in phantom, extend through the entire length of the handpiece. The suction lumen 22 is connectible to the suction source 18 at one end and terminates at a suction port 28 at the other end. The irrigation lumen 24 is connectible to the irrigation source 12 at one end and terminates at an irrigation port 30 at the other end. Both ports 28 and 30 are formed through a fitting 26 at the distal end of the handpiece 10.

In accordance with principles of the invention, a special tip (i.e. tip 16) is provided for use with the conventional handpiece 10. The proximal end of the tip 16 is configured to detachably mate with the fitting 26. When the tip 16 is connected to the handpiece 10 and the handpiece 10 is energized (by squeezing a trigger 31), irrigation fluid passes through the irrigation port 30 and into the tip 16. The irrigation fluid is emitted in a pulsatile liquid stream from the distal end 32 of the tip at a pulsating frequency that is controllable by the trigger 31. However, the suction port 28 is plugged by a plug 34 extending from the tip proximal end 36. When the tip 16 is not connected to the handpiece 10, a plug 38 having two projections 40, 44 preferably is inserted into the ports 28 and 30 to prevent entry of contaminants into the handpiece.

Figure 3:
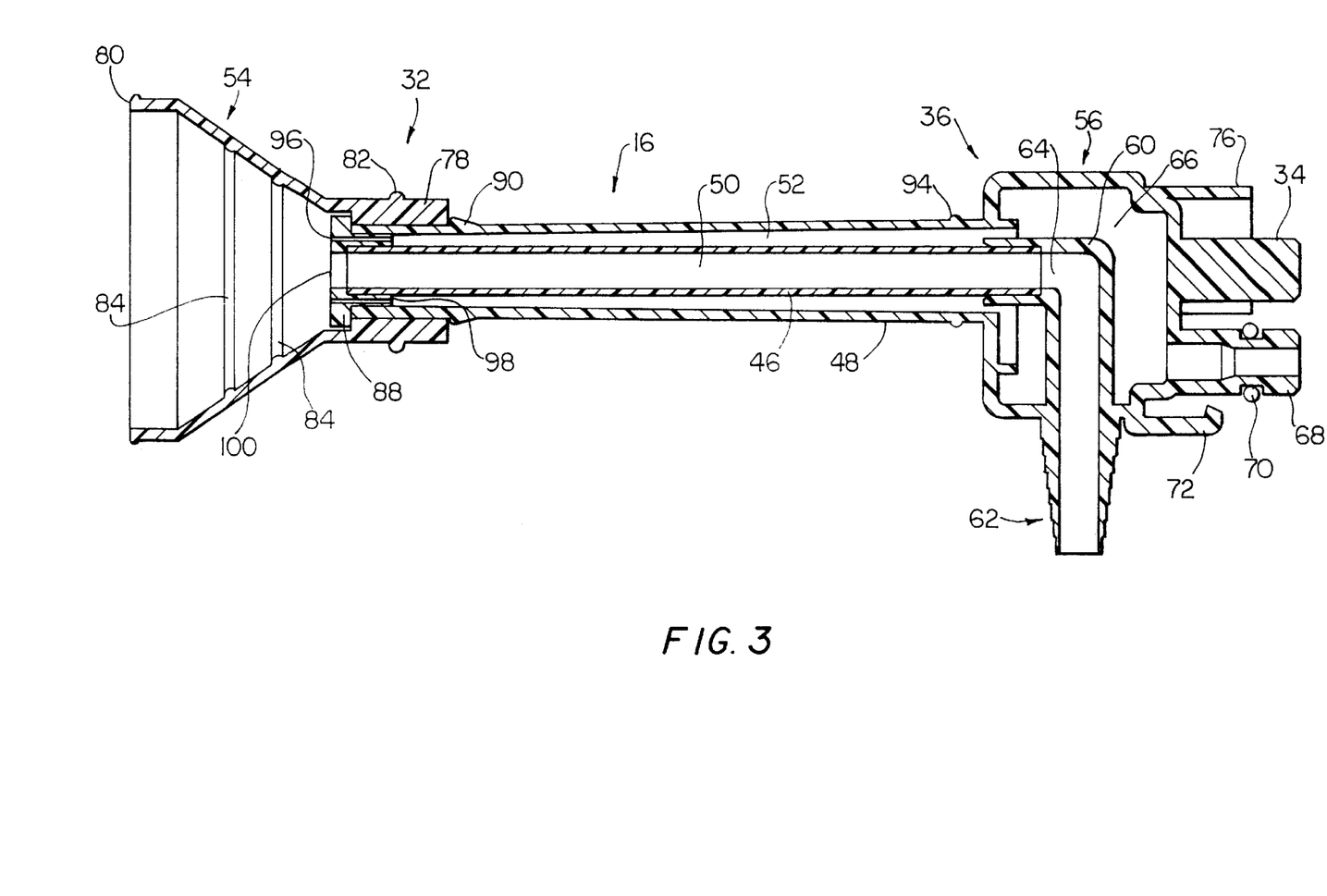
FIG. 3 is a longitudinal cross section of the suction irrigation tip along line 3—3 of FIG. 1.

The tip 16, illustrated in cross section in FIG. 3. may be made from a hard, substantially transparent plastic. The tip 16 includes an inner (suction) tube 46 coaxially aligned within an outer (irrigation) tube 48, a flexible, funnel-shaped splash shield 54, and a connector 56. The suction tube 46 provides a direct pathway 50 for suction from the tip distal end 32 to a suction source (schematically illustrated as source 18 in FIG. 1). Aspirated debris therefore never enters the handpiece 10. The annular space 52 between the suction and irrigation tubes 46 and 48 provides a pathway for irrigation fluid. The splash shield 54, slidably mounted to the irrigation tube 48, enables treatment to be confined to a localized treatment site. The connector 56 at the tip proximal end 36 removably connects the tip 16 to the handpiece 10.

Figure 5:
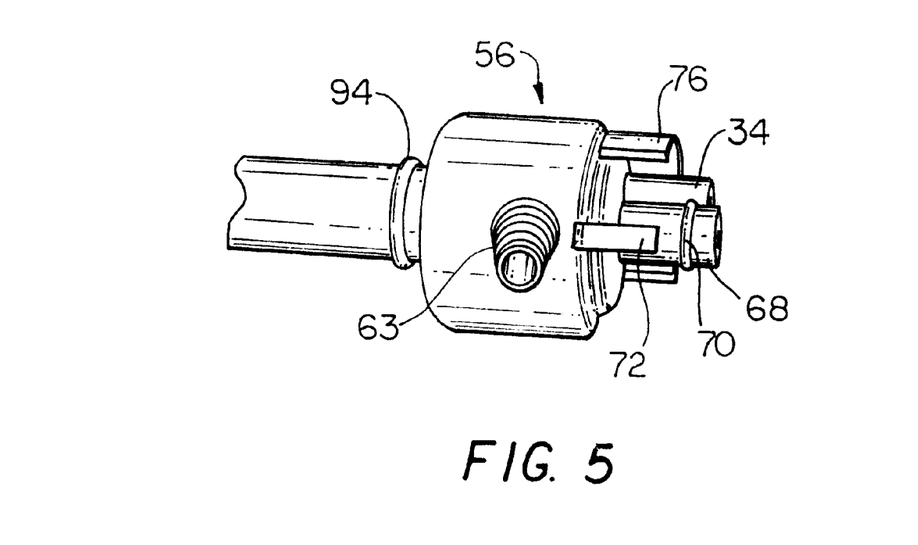
FIG. 5 is a bottom perspective view of the rear portion of the suction irrigation tip.

The suction tube 46 is supported within the irrigation tube 48 at one end by an outlet nozzle 58, and at the other end by an elbow shaped conduit 60. The outlet nozzle 58 is in the form of a plurality of circumferentially spaced openings formed in an annular end wall. The elbow shaped conduit 60 extends into and downwardly through the connector 56, terminating at a tapered lower end 62 having a plurality of annular ridges 63 (FIG. 5). The suction tube 46 is sealed to both the outlet nozzle 58 and elbow-shaped conduit 60 to form a continuous suction lumen 64 from the tip distal end 32 to the tapered lower end 62 of the elbow 60 to which the suction tubing 20 from a suction source may be connected.

Although the elbow shaped conduit 60 is shown as extending from the proximal end of the suction tube 46, it may depend from any part of the suction tube 46. In an alternative embodiment, for example, the suction tube 46 is about half the size as it is in the preferred embodiment and the elbow shaped conduit 60 may connect to the suction tube 46 within the irrigation tube 48. The tapered end 62 of the elbow shaped conduit 60 extends through a wall of the irrigation tube 48 for connection with the flexible suction tubing 20.

The connector 56 has an irrigation fluid chamber 66 that receives fluid from the handpiece irrigation port 30 through an irrigation connector 68. After the fluid is received in the fluid chamber 66, the fluid chamber 66 directs it to the annular space 52, which then directs it through the outlet nozzle 58. An O-ring 70 may encircle the irrigation connector 68 to seal the connection between the irrigation connector 68 and the irrigation port 30 on the handpiece. A flexible clip 72 may be molded integrally with the connector 56 for engagement with a lip 74 formed along the underside of the handpiece fitting 26.

Figure 4:
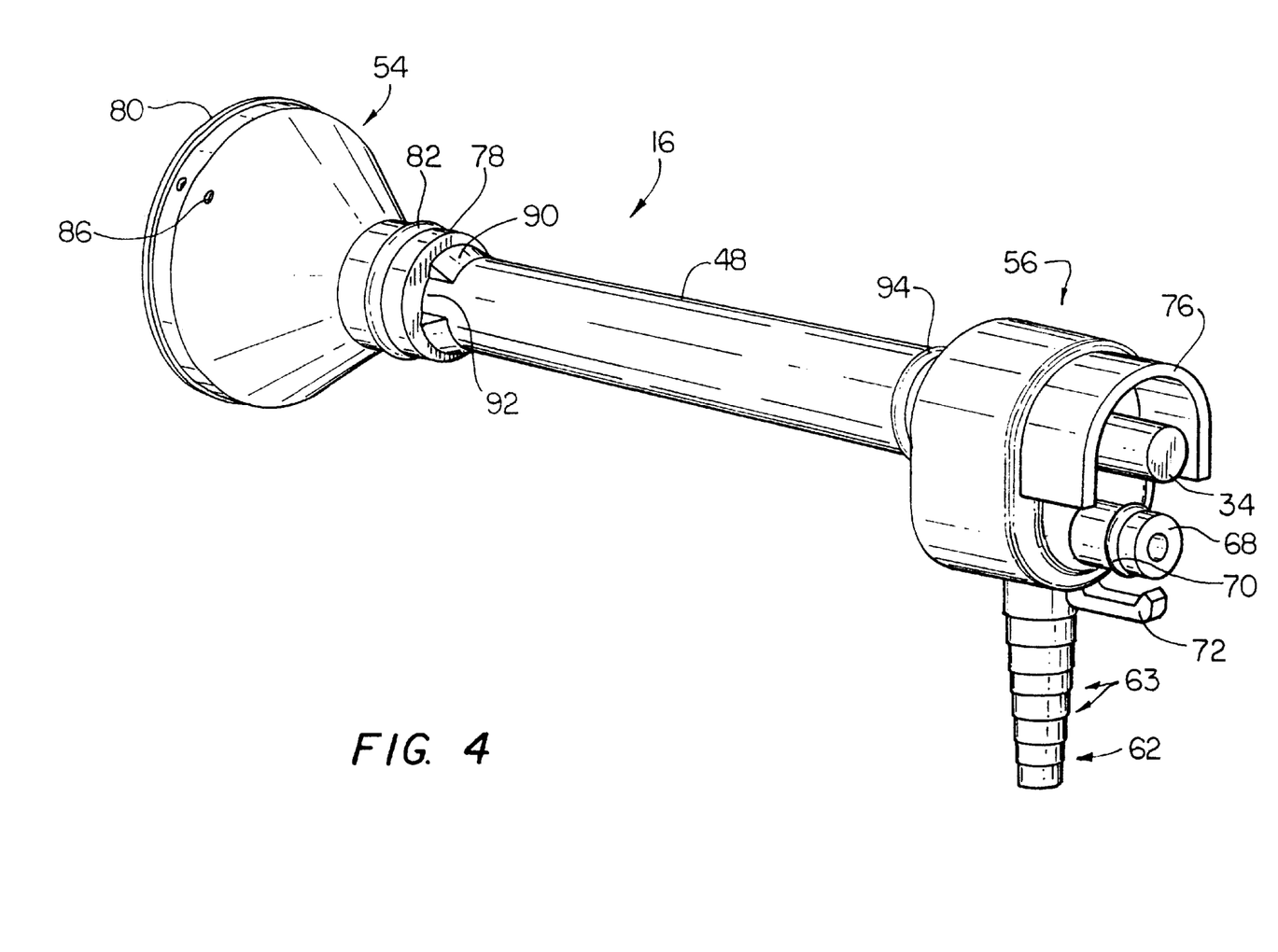
FIG. 4 is a perspective view of the suction irrigation tip showing the rear and side components of the tip.

As shown in FIGS. 4 and 5, a hood 76 extends proximally from the connector 56 to shield the suction and irrigation ports 28 and 30 from irrigation fluid and debris that, in use, may splash back toward the handpiece 10. The hood 76 preferably has a partially oblong shape, approximating the shape of the handpiece fitting 26. It extends downwardly about the tip plug 34 and partially about the irrigation connector 68. When the tip 16 is connected to the handpiece 10, the hood 76 covers the top portion of the fitting 26, thus further reducing the risk of splashed fluids contaminating the ports 28 and 30. The rounded top of the hood 76 causes fluids to drip past the sides of the nozzle 26.

The flexible shield 54 includes a proximal collar 78 and a conical body that diverges in a distal direction to a distal rim 80. The collar 78 is slidably mounted to the irrigation tube 48 and has an annular gripping ridge 82 to facilitate gripping the collar 78. A plurality of circumferential ridges 84 (e.g., three) may be included on the inner surface of the shield 54 to serve as cutting guides for cutting shield 54. Vent holes 86 formed in the side of the shield 54 prevent the shield 54 from collapsing under suction and also enable air to mix with the debris aspirated from the site to avoid stagnation of the debris within the shield 54. The shield 54 may be made from a flexible, substantially clear plastic that may be shaped during use to conform to the shape and contour of the irrigation site.

The collar 78 may be secured to the distal end of the tip 16 by both an annular flange 88 (shown in FIGS. 2 and 3) and a discontinuous circumferential ridge 90 formed on the irrigation tube 48. The ridge 90 has two discontinuities 92 that enable the shield 54 to be easily forced over the securing ridge 90. The shield 54 may be retracted proximally (FIG. 2), over the securing ridge 90, by applying a proximal force to either the rim 54 or to the gripping ridge on the collar 78. The irrigation tube 48 may be tapered slightly toward the tip distal end 32 to increase the resistance to proximally retracting the shield 54. A stop ridge 94 may circumscribe the proximal end of the irrigation tube 48 to prevent the splash shield 54 from being retracted into contact with the connector 56.

Figure 6:
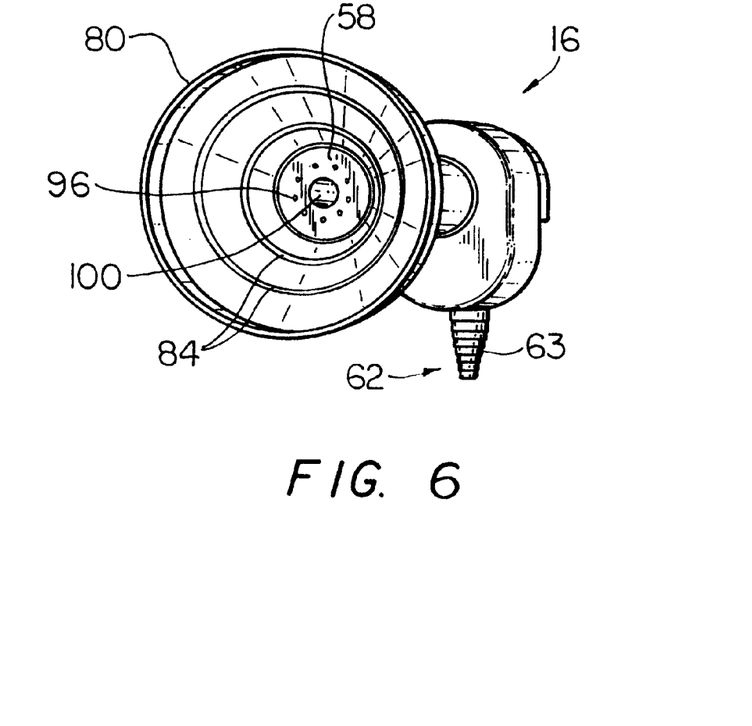
FIG. 6 is a front perspective view of the suction irrigation tip.

The shower head nozzle 58 is fastened to the tip distal end 32 and includes an end wall 97 and a cylindrical wall 98 extending proximally from the end wall. The nozzle 58 serves a number of important functions. In addition to partially securing the splash shield 54 to the tip 16 and securing the suction tube 46 coaxially within the irrigation tube 48, it can be configured to emit irrigation fluid from the tip 16 in a specialized spray pattern. To that end, the shower head nozzle 58 has a plurality of irrigation holes 96 (e.g., nine) longitudinally formed through the cylindrical wall 98 and end wall 97, and a central suction hole 100. The diameter of the central suction hole 100 should have approximately the same diameter as the inner diameter of the suction tube 46 such as, for example, 0.1875 inches. The number, shape, and size of the irrigation holes 96 are selected both to provide a specialized spray pattern for the irrigation fluid and to regulate the force with which the irrigation fluid is emitted from the tip 16. Accordingly, the suction/irrigation tip 16 may be customized to be usable with certain handpieces only. For example, when irrigating an externally exposed wound (e.g., a bed sore), it is preferred that the irrigation fluid be emitted from the tip 16 at a force not exceeding 15 p.s.i. When the tip 16 is used with the Simpulse Solo™ suction irrigation handpiece, nine round holes having a diameter of 0.040 inches have produced satisfactory results. Similarly, when used with the Simpulse Plus™ suction irrigation handpiece, also available from C.R. Bard, Inc., four round holes having a diameter of 0.040 inches have produced satisfactory results.

During the irrigation procedure, it therefore is important that the attendant easily select the tip 16 that corresponds with a specific handpiece 10. Accordingly, it is preferred that the tip 16 have a simple identification means that quickly and easily indicates the tip 16 that corresponds to the handpiece 10 being used. To that end, the tip connector 56 may be color coded to correlate with the handpiece 10. For example, the tip connector 56 to be used with the Simpulse Solo™ may be colored purple, while the tip connector 56 to be used with the Simpulse Plus™ may be colored green. As a further means for ensuring proper tip use, the tip connector 56 may be specially shaped to mate only with the fitting 26 of the handpiece 10 with which it is to be used. Therefore, the wrong tip 16 cannot fit into the wrong pump/handpiece 10. To that end, either the irrigation connector 68 or the tip plug 34 may be provided with a ridge 101 (FIG. 4) or other irregularity, and the corresponding handpiece suction port 28 or irrigation port 30 may be molded to that complimentary shape. The connector 56 may only be connected to the corresponding port for a fluid tight fit.

Figure 7:
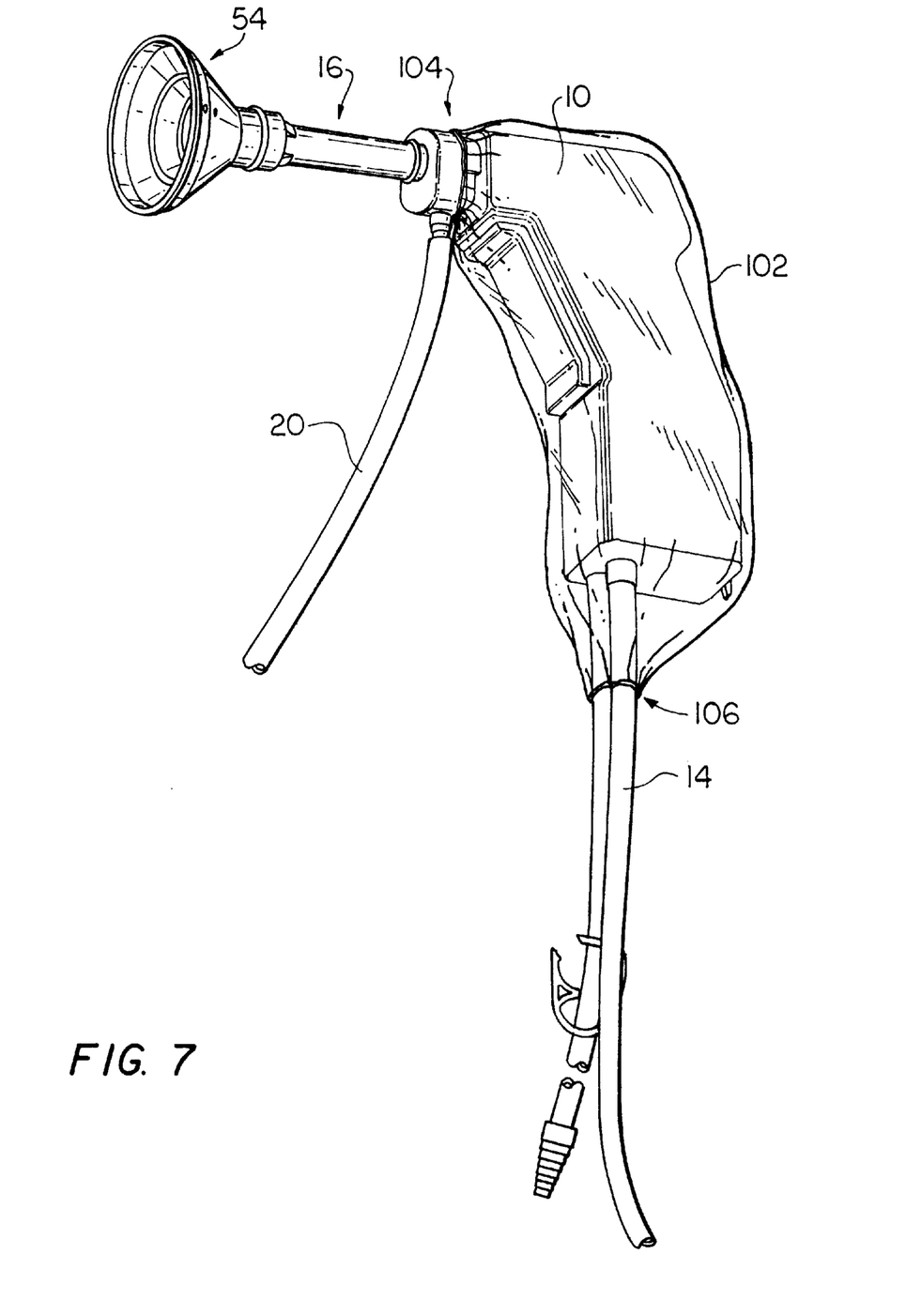
FIG. 7 is a perspective view of the suction irrigation tip and handpiece with the polymeric envelope extending just past the bottom of the handpiece.

FIG. 7 illustrates an arrangement by which the handpiece 10 is protected from irrigation fluid and other biological debris that may splash from the irrigation site during use. To that end, the tip 16 is provided with an protective covering 102 having one end 104 that is heat sealed to the connector 56 and another end 106 that is open. The protective covering 102 is sized to fit loosely about the handpiece 10. The length of the protective covering 102 preferably is long enough to extend to the bottom end of the handpiece 10. This ensures that the handpiece 10 will remain protected by the protective covering 102 even though the protective covering 102 might shift somewhat relative to the handpiece 10. An elastic band may be connected about the protective covering open end 106 to provide a secure fit about the bottom end of the handpiece 10. The protective covering 102 is can be made from a thin, flexible, substantially transparent polymeric material, such as a low density polyethylene having a thickness of about 0.001 inch. It is dimensioned so that it will maintain a loose fit about the handpiece 10. The flexibility and transparent nature of the polymeric protective covering 102 enables the attendant to effectively operate all the controls on the handpiece 10 through the protective covering.

Figure 8:
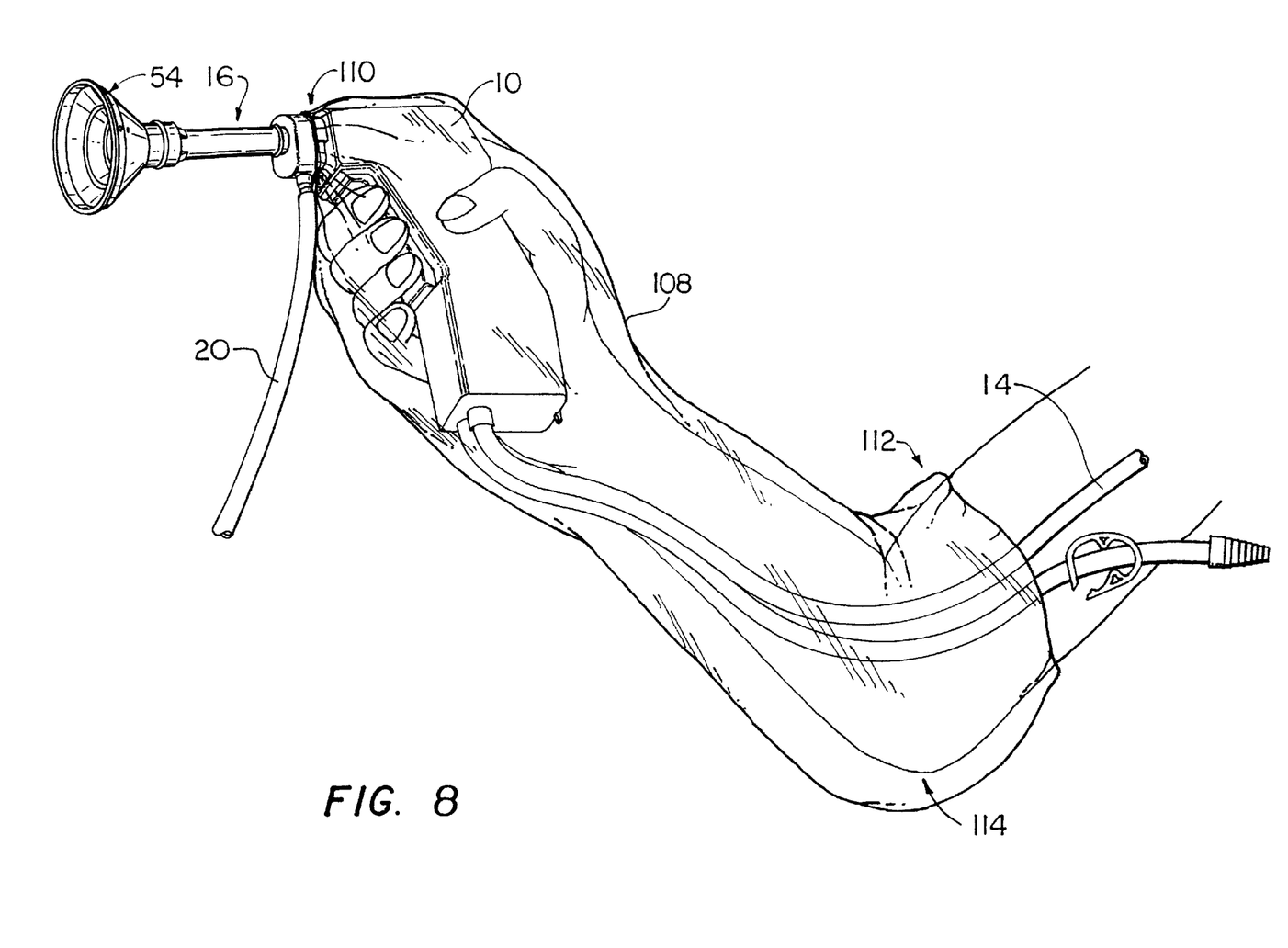
FIG. 8 is a perspective view of the suction irrigation tip and handpiece with the polymeric envelope extending to the attendant's elbow.

FIG. 8 shows a second arrangement by which both the handpiece 10 and attendant's arm are protected from debris that splashes from the site. To that end, the tip 16 is provided with a long protective covering 108 having one end 110 that is heat sealed to the connector 56 and another end 112 that is open. The long protective covering 108 is sized to fit loosely about the handpiece 10 so that the attendant may operate the handpiece 10 from within the long protective covering 108. The length of the protective covering 108 preferably is three times the length of the handpiece 10 so that the open end 112 will extend approximately to the attendant's elbow 114. This ensures that both the handpiece 10 and attendant's arm will be protected from debris that splashes from the site. The long protective covering 108 may be made from a thin, flexible, substantially transparent polymeric material, such as a low density polyethylene having a thickness of about 0.001 inch. It is dimensioned so that the attendant's hand will easily fit inside the protective covering 108 to operate the handpiece 10. The flexibility and transparent nature of the long protective covering 108 enables the attendant to effectively operate all the controls on the handpiece 10 from inside and outside the protective covering 108.

When in use, the tip 16 is connected to the handpiece 10 and the flexible suction tubing 20 is connected to the tapered lower end 62 of the elbow shaped conduit 60. The handpiece suction tube 22 remains unused. Since the tip 16 is connected to the handpiece 10, the tip plug 34 sealingly connects to the handpiece suction port 28 and the irrigation connector 68 connects to the handpiece irrigation port 30. The shield 54 may be positioned at the tip distal end 32 and the rim 80 may positioned at the local irrigation site. If desired, either of the flexible protective coverings 102 or 108 may be disposed over and about the handpiece 10. The user may then simultaneously irrigate and aspirate the site. The attendant may retract the shield 54 to put the shower head nozzle 58 directly against, or very close proximity to, the irrigated site. The large cross-sectional area of the suction tube 46 reduces the possibility of clogging. After use, the tip 16 and protective covering 102 or 108 are discarded and the two prong plug 38 is inserted into the suction and irrigation ports 28, 30 to ensure that the handpiece 10 remains aseptic. The handpiece 10 may be reused at a later time by removing the two prong plug 38 and inserting a new suction irrigation tip 16.

It should be understood that the foregoing description of the invention is intended merely to be illustrative thereof and that other modifications and embodiments may be apparent to those skilled in the art without departing from its spirit.

Having thus described the invention, what we desire to claim and secure by Letters Patent is:

1. A detachable suction tip for use with a suction handpiece, the handpiece having a suction lumen extending therethrough for removing irrigation fluid from an irrigation site, the tip comprising:
   a suction tube for aspirating irrigation fluid from the irrigation site, the suction tube having a fluid bypass path within the detachable tip which channels aspirated irrigation fluid directly to a suction source so that aspirated fluid within the suction tube does not enter the handpiece suction lumen;
   a connector for mechanically connecting the tip to the handpiece, the connector also having a plug for sealing the suction lumen in the handpiece;
   an irrigation tube for directing the irrigation fluid to the irrigation site, the suction tube being within the irrigation tube.

2. A detachable suction and irrigation tip for use with an irrigation handpiece, the handpiece having a suction lumen and an irrigation lumen extending therethrough, the irrigation lumen directing irrigation fluid to an irrigation site, the tip comprising:
   an irrigation tube for directing the irrigation fluid to the irrigation site;
   a connector for detachably connecting the irrigation tube to the handpiece to provide fluid communication therebetween and for sealing the suction lumen in the handpiece; and
   a suction tube for aspirating irrigation fluid from the irrigation site, the irrigation tube and suction tube being coaxially aligned, the suction tube having a fluid bypass path within the detachable tip which channels aspirated irrigation fluid directly to a suction source so that aspirated fluid within the suction tube does not enter the handpiece.

3. A detachable suction and irrigation tip for use with an irrigation handpiece, the handpiece having a suction lumen and an irrigation lumen extending therethrough, the irrigation lumen directing irrigation fluid to an irrigation site, the tip comprising:
   an irrigation tube for directing the irrigation fluid to the irrigation site;
   a connector for detachably connecting the irrigation tube to the handpiece to provide fluid communication therebetween and for sealing the suction lumen in the handpiece; and
   a suction tube for aspirating irrigation fluid from the irrigation site, the suction tube being disposed in the irrigation tube, the suction tube having a fluid bypass path within the detachable tip which channels aspirated irrigation fluid directly to a suction source so that aspirated fluid within the suction tube does not enter the handpiece.

4. The tip as defined by claim 3 wherein the fluid bypass path passes through the irrigation tube.

5. A detachable suction and irrigation tip for use with an irrigation handpiece, the handpiece having a suction lumen and an irrigation lumen extending therethrough, the irrigation lumen directing irrigation fluid to an irrigation site, the tip comprising:
   an irrigation tube for directing the irrigation fluid to the irrigation site;
   a connector for detachably connecting the irrigation tube to the handpiece to provide fluid communication therebetween and for sealing the suction lumen in the handpiece; and
   a suction tube for aspirating irrigation fluid from the irrigation site, the suction tube having a fluid bypass path within the detachable tip which channels aspirated irrigation fluid directly to a suction source so that aspirated fluid within the suction tube does not enter the handpiece; and
   a splash shield slidably mounted on the tip.

6. A detachable suction and irrigation tip for use with an irrigation handpiece, the handpiece having a suction lumen and an irrigation lumen extending therethrough, the irrigation lumen directing irrigation fluid to an irrigation site, the tip comprising:
   an irrigation tube for directing the irrigation fluid to the irrigation site;
   a connector for detachably connecting the irrigation tube to the handpiece to provide fluid communication therebetween and for sealing the suction lumen in the handpiece; and
   a suction tube for aspirating irrigation fluid from the irrigation site, the suction tube having a fluid bypass path within the detachable tip which channels aspirated irrigation fluid directly to a suction source so that aspirated fluid within the suction tube does not enter the handpiece; and
   a fluid deflecting hood extending from the connector to deflect splashed irrigation fluid away from the handpiece.

7. A detachable suction and irrigation tip for use with an irrigation handpiece, the handpiece having a suction lumen and an irrigation lumen extending therethrough, the irrigation lumen directing irrigation fluid to an irrigation site, the tip comprising:
   an irrigation tube for directing the irrigation fluid to the irrigation site;
   a connector for detachably connecting the irrigation tube to the handpiece to provide fluid communication therebetween and for sealing the suction lumen in the handpiece; and
   a suction tube for aspirating irrigation fluid from the irrigation site, the suction tube having a fluid bypass path within the detachable tip which channels aspirated irrigation fluid directly to a suction source so that aspirated fluid within the suction tube does not enter the handpiece; and
   a protective covering fastened to the tip and covering the handpiece.

8. A detachable suction and irrigation tip for use with an irrigation handpiece, the handpiece having a suction lumen and an irrigation lumen extending therethrough, the irrigation lumen directing irrigation fluid to an irrigation site, the tip comprising:
   an irrigation tube for directing the irrigation fluid to the irrigation site;
   a connector for detachably connecting the irrigation tube to the handpiece to provide fluid communication therebetween and for sealing the suction lumen in the handpiece; and
   a suction tube for aspirating irrigation fluid from the irrigation site, the suction tube having a fluid bypass path within the detachable tip which channels aspirated irrigation fluid directly to a suction source so that aspirated fluid within the suction tube does not enter the handpiece; and the suction tube having a tube segment that diverts aspirated fluid away from the distal end of the handpiece.

9. A method of irrigating an irrigation site, the method comprising the steps of:
   (a) providing a handpiece defining a handpiece irrigation lumen and a handpiece suction lumen;
   (b) connecting the handpiece irrigation lumen to an irrigation fluid source;
   (c) detachably connecting a tip to the distal end of the handpiece, the tip having a tip irrigation tube in fluid communication with the handpiece irrigation lumen, a tip suction tube for aspirating fluid from the site and a bypass fluid path in fluid communication with the tip suction tube, and
   (d) connecting the bypass fluid path to a suction source.

10. The method of irrigating the irrigation site as defined by claim 9 wherein step (c) comprises the step of plugging the handpiece suction lumen.

11. The method of irrigating the irrigation site as defined by claim 9 further comprising the steps of:
   (e) removing the tip from the handpiece;
   (f) inserting a plug in the handpiece suction lumen; and
   (g) inserting a plug in the handpiece irrigation lumen.

12. The method of irrigating the irrigation site as defined by claim 9 further comprising the steps of:
   (h) removing the plug from the handpiece suction lumen;
   (i) removing the plug from the handpiece irrigation lumen; and
   (j) connecting a second tip to the handpiece, the second tip having a tip irrigation tube, and a tip suction tube that prevents aspirated fluid from communicating with the handpiece suction lumen.

13. An apparatus for irrigating an irrigation site comprising:
   a handpiece having a lower end;
   a tip connected to the handpiece and having a proximal end; and
   a flexible protective covering connected to the tip, the protective covering disposed about and surrounding the proximal end of the tip and the handpiece, the protective covering extending at least to the lower end of the handpiece.

14. The apparatus as defined by claim 13 wherein the protective covering has a length of approximately three times the length of the handpiece.

* * * * *

UNITED STATES PATENT AND TRADEMARK OFFICE
CERTIFICATE OF CORRECTION

PATENT NO. : 6,200,292 B1  Page 1 of 1
DATED : March 13, 2001
INVENTOR(S) : Glen French et al.

It is certified that error appears in the above-identified patent and that said Letters Patent is hereby corrected as shown below:

<u>Title page,</u>
The following U.S. PATENT DOCUMENTS under Item [56], References Cited should be added:
-- 4,692,140   09/1987   Olson
5,030,202   07/1991   Harris
5,170,779   12/1992   Ginsberg
5,460,604   10/1995   Arnett et al.
5,464,390   11/1995   Arnett et al.
5,496,290   03/1996   Ackerman --

Signed and Sealed this

Sixteenth Day of July, 2002

*Attest:*

*Attesting Officer*

JAMES E. ROGAN
*Director of the United States Patent and Trademark Office*

(12) EX PARTE REEXAMINATION CERTIFICATE (5001st)
United States Patent
French et al.

(10) Number: US 6,200,292 C1
(45) Certificate Issued: Oct. 19, 2004

(54) SUCTION AND IRRIGATION HANDPIECE AND TIP (75) Inventors: Glen French, Barrington, RI (US); Stephen Albrecht, South Walpole, MA (US); Roger Darois, Foster, RI (US); Robert Sakal, Riverside, RI (US); Laurence Tremaine, West Warwick, RI (US)

(73) Assignee: C. R. Bard, Inc., Murray Hill, NJ (US)

Reexamination Request:
No. 90/006,388, Sep. 23, 2002

Reexamination Certificate for:
Patent No.: 6,200,292
Issued: Mar. 13, 2001
Appl. No.: 08/665,467
Filed: Jun. 18, 1996

Certificate of Correction issued Jul. 16, 2002.

(51) Int. Cl.[7] .................. A61M 1/00; A61M 37/00
(52) U.S. Cl. .................................. 604/131; 604/35
(58) Field of Search ......................... 604/131–133, 604/146, 151, 153, 43, 35, 39, 310, 313, 355, 268, 27, 28, 30, 36, 147, 149, 902

(56) References Cited

U.S. PATENT DOCUMENTS

| | | |
|---|---|---|
| 517,274 A | 3/1894 | Gullings |
| 906,711 A | 12/1908 | McClung Hill et al. |
| 1,178,898 A | 4/1916 | Young |
| 1,889,425 A | 11/1932 | Sorenson |
| 2,531,793 A | 11/1950 | Sulek |
| 2,771,072 A | 11/1956 | De Montauge |
| 3,735,751 A | 5/1973 | Katz |
| RE28,405 E | 5/1975 | Sollerud |
| 4,519,385 A | 5/1985 | Atkinson et al. |
| 4,692,140 A | 9/1987 | Olson |
| 4,776,840 A | 10/1988 | Freitas et al. |
| 4,810,194 A | 3/1989 | Snedden |
| 5,030,202 A | 7/1991 | Harris |
| 5,046,486 A | 9/1991 | Grulke et al. |
| 5,170,779 A | 12/1992 | Ginsberg |
| 5,302,124 A | 4/1994 | Lansing et al. |
| 5,354,267 A | 10/1994 | Niermann et al. |
| 5,460,604 A | 10/1995 | Arnett et al. |
| 5,464,390 A | 11/1995 | Arnett et al. |
| 5,470,305 A | 11/1995 | Arnett et al. |
| 5,488,949 A | 2/1996 | Kreifels et al. |
| 5,496,290 A | 3/1996 | Ackerman |
| 5,527,275 A | 6/1996 | Ginsberg |
| 5,735,833 A | 4/1998 | Olson |
| 5,746,721 A | 5/1998 | Pasch et al. |
| 5,941,851 A | 8/1999 | Coffey et al. |

FOREIGN PATENT DOCUMENTS

| | | |
|---|---|---|
| GB | 2171312 | 8/1986 |
| WO | WO 95/01759 | 1/1995 |

*Primary Examiner*—Brian L. Casler (57) ABSTRACT

A medical suction and irrigation apparatus includes a suction/irrigation tip removably connected to a conventional suction/irrigation handpiece. Suction is provided through a suction tube which has a bypass conduit in the tip. The bypass conduit is directly connectable to a suction source so that aspirated debris passes through the tip to the suction source. The suction tube thus prevents aspirated debris from entering the conventional suction tube in the handpiece and contaminating the handpiece. The suction tube is also designed to have a maximum size to prevent the tip from clogging. The tip also has an irrigation tube for directing irrigation liquid to the irrigation site, and a connector which connects the irrigation tube to the handpiece so that the handpiece pumps fluid through the tip in a conventional manner. A flexible splash shield, slidably mounted to the irrigation tube, confines irrigation fluid to the local site.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

\* \* \* \* \*